(12) United States Patent
Weinberg et al.

(10) Patent No.: US 11,612,510 B2
(45) Date of Patent: Mar. 28, 2023

(54) DRAINABLE OSTOMY POUCH

(71) Applicant: Hollister Incorporated, Libertyville, IL (US)

(72) Inventors: Robert J. Weinberg, Lake Villa, IL (US); Timothy A. Friske, Round Lake Beach, IL (US); Christina Augustyn, Chicago, IL (US); Ronald S. Botten, Gurnee, IL (US)

(73) Assignee: Hollister Incorporated, Libertyville, IL (US)

( * ) Notice: Subject to any disclaimer, the term of this patent is extended or adjusted under 35 U.S.C. 154(b) by 478 days.

(21) Appl. No.: 16/473,208

(22) PCT Filed: Jan. 19, 2018

(86) PCT No.: PCT/US2018/014517
§ 371 (c)(1),
(2) Date: Jun. 24, 2019

(87) PCT Pub. No.: WO2018/136793
PCT Pub. Date: Jul. 26, 2018

(65) Prior Publication Data
US 2019/0328572 A1    Oct. 31, 2019

Related U.S. Application Data

(60) Provisional application No. 62/448,612, filed on Jan. 20, 2017.

(51) Int. Cl.
*A61F 5/44* (2006.01)
*A61F 5/445* (2006.01)
*A61L 28/00* (2006.01)

(52) U.S. Cl.
CPC ............ *A61F 5/4407* (2013.01); *A61F 5/445* (2013.01); *A61L 28/00* (2013.01)

(58) Field of Classification Search
CPC ......... A61F 5/4407; A61F 5/445; A61L 28/00
(Continued)

(56) References Cited

U.S. PATENT DOCUMENTS 3,523,534 A    8/1970    Nolan
4,411,659 A   10/1983    Jensen et al.
(Continued)

FOREIGN PATENT DOCUMENTS

GB    2346328 B  * 12/2003  ........... A61F 5/4407
JP    S64500487 A    2/1989
(Continued)

OTHER PUBLICATIONS

International Preliminary Report on Patentability issue by International Bureau in connection with PCT/US2018/014517 dated Aug. 1, 2019.
(Continued)

*Primary Examiner* — Susan S Su
*Assistant Examiner* — Ted Yang
(74) *Attorney, Agent, or Firm* — Levenfeld Pearlstein, LLC

(57) ABSTRACT

A drainable ostomy pouch outlet includes a single-piece closure member including at least one transversely-extending fold-line. The at least one transversely-extending fold-lines are configured to facilitate folding up and closing of the outlet. The single-piece closure member may also include at least one axially-extending or slanted fold-lines intersecting the at least one transversely-extending fold-line, configured to facilitate opening of the outlet.

18 Claims, 6 Drawing Sheets

(58) Field of Classification Search
USPC .................................................. 604/335, 332
See application file for complete search history.

(56) References Cited

U.S. PATENT DOCUMENTS

| | | | |
|---|---|---|---|
| 4,592,750 A | | 6/1986 | Kay |
| 5,065,459 A * | | 11/1991 | Tjahaja .................... A61F 5/44 |
| | | | 4/144.2 |
| 5,968,024 A * | | 10/1999 | Freeman ............... A61F 5/4407 |
| | | | 604/323 |
| 6,019,770 A * | | 2/2000 | Christoudias .... A61B 17/00234 |
| | | | 604/403 |
| 6,336,918 B1 * | | 1/2002 | Olsen .................... A61F 5/4407 |
| | | | 604/355 |
| 7,879,015 B2 | | 2/2011 | Villefrance et al. |
| 8,672,907 B2 | | 3/2014 | Friske et al. |
| 8,821,463 B2 * | | 9/2014 | Grum-Schwensen ....................... |
| | | | A61F 5/443 |
| | | | 604/332 |
| 2003/0073962 A1 * | | 4/2003 | Olsen .................... A61F 5/445 |
| | | | 604/327 |
| 2003/0153882 A1 * | | 8/2003 | Mandzij ............... A61F 5/4407 |
| | | | 604/334 |
| 2003/0167042 A1 * | | 9/2003 | Poulsen ............... A61F 5/4407 |
| | | | 604/327 |
| 2005/0131360 A1 * | | 6/2005 | Villefrance ............. A61F 5/445 |
| | | | 604/332 |
| 2010/0152686 A1 * | | 6/2010 | Ryder .................. A61F 5/4407 |
| | | | 604/332 |
| 2012/0022478 A1 * | | 1/2012 | Friske .................. A61F 5/4407 |
| | | | 604/335 |
| 2013/0253456 A1 * | | 9/2013 | Friske ..................... A61F 5/445 |
| | | | 604/332 |
| 2020/0046543 A1 * | | 2/2020 | Scalise .................. A61F 5/4405 |

FOREIGN PATENT DOCUMENTS

| | | | | |
|---|---|---|---|---|
| JP | 2002518128 A | 6/2002 | | |
| JP | 3131250 U | 4/2007 | | |
| WO | WO-2006031275 A2 * | 3/2006 | ........... | A61F 5/4407 |
| WO | 2013022575 A1 | 2/2013 | | |
| WO | 2014181338 A2 | 11/2014 | | |
| WO | 2017001846 A1 | 1/2017 | | |

OTHER PUBLICATIONS

Written Opinion issued by ISA/EPO in connection with PCT/US2018/014517 dated May 7, 2018.
International Search Report issued by ISA/EPO in connection with PCT/US2018/014517 dated May 7, 2018.

* cited by examiner

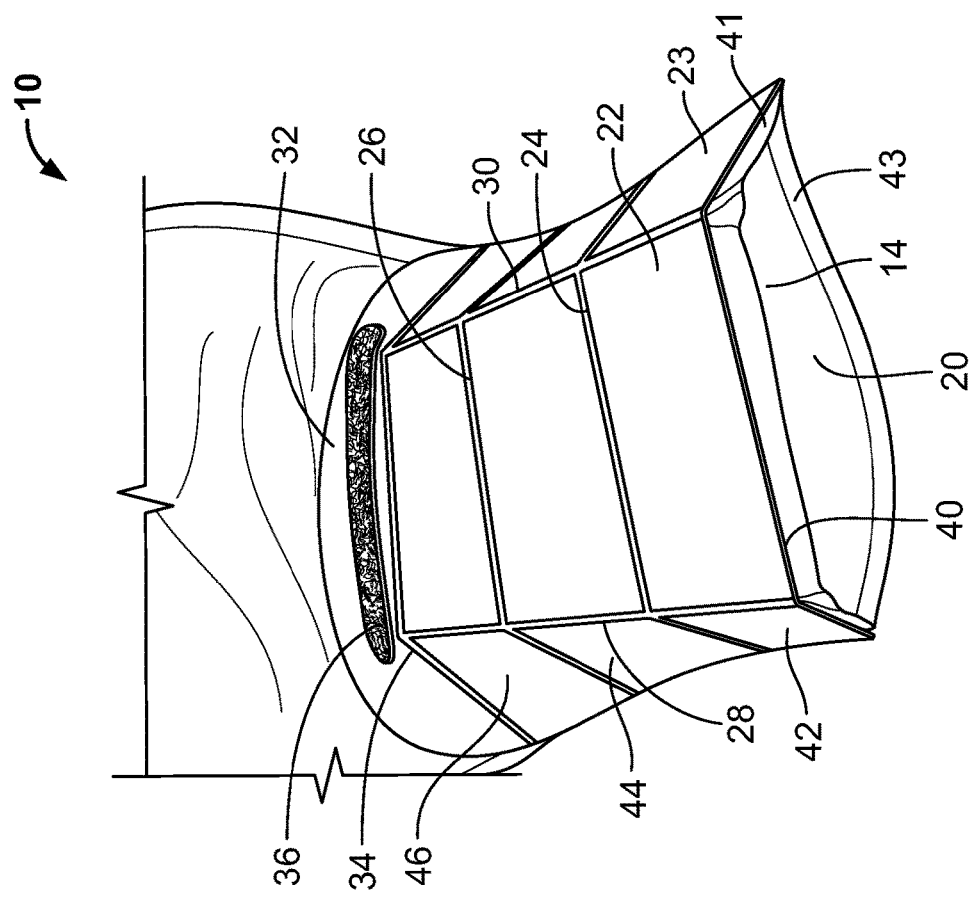
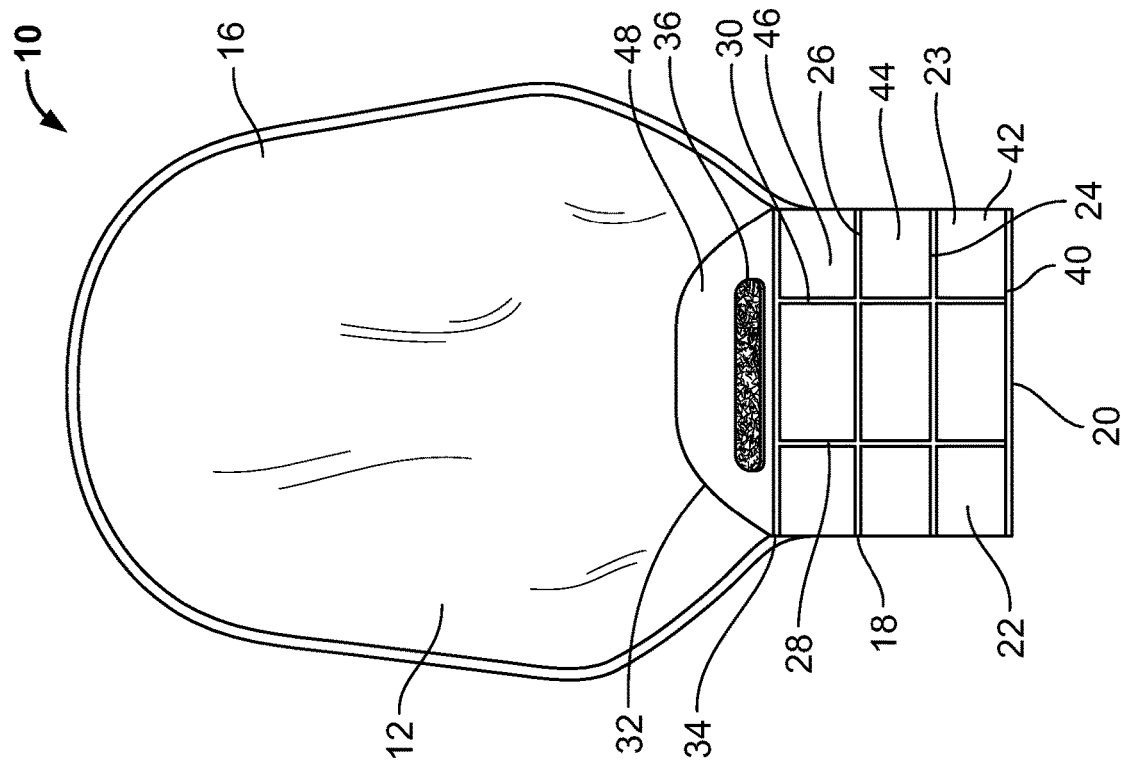

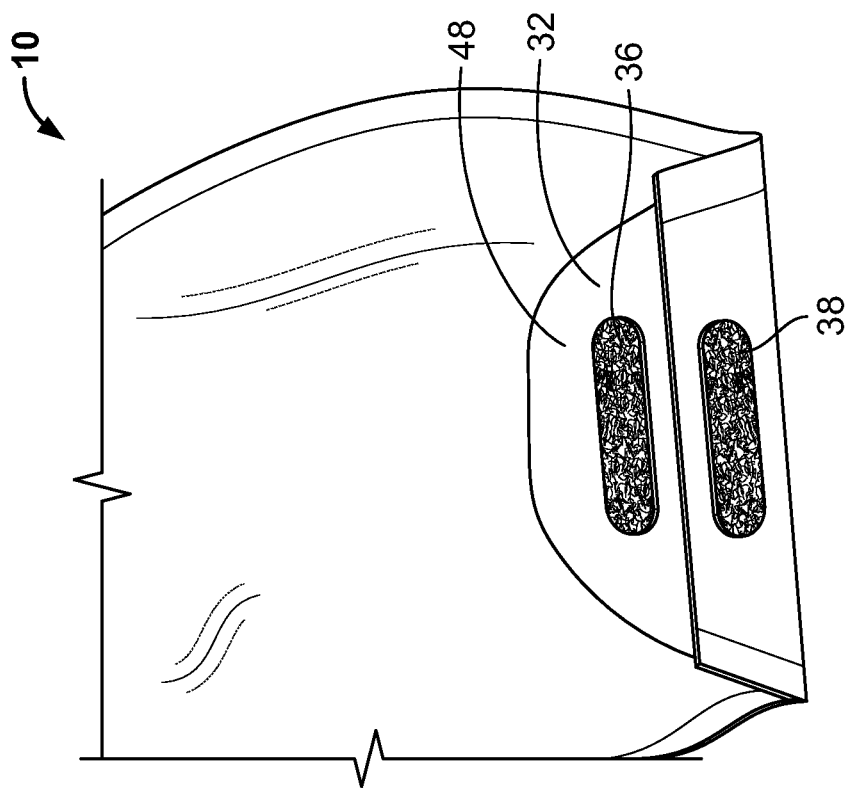
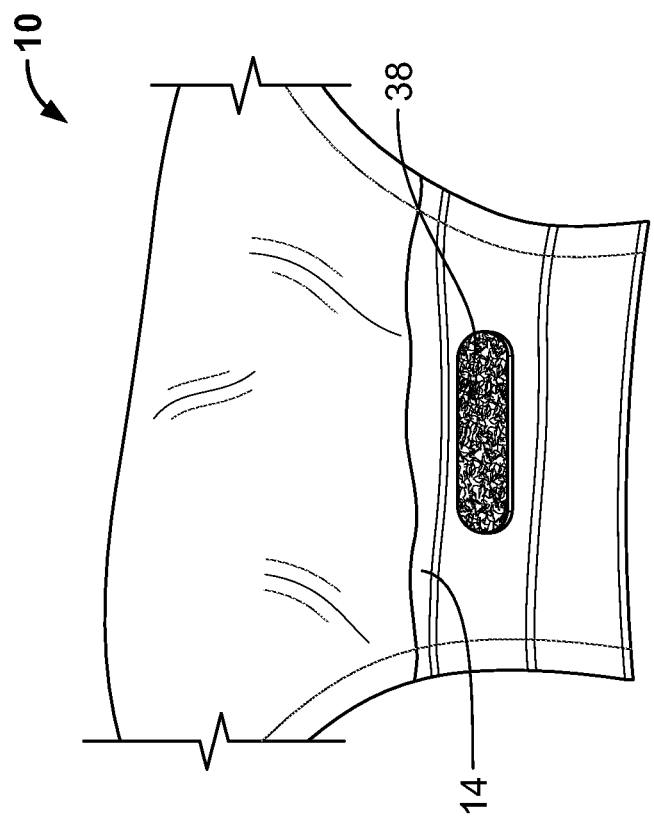

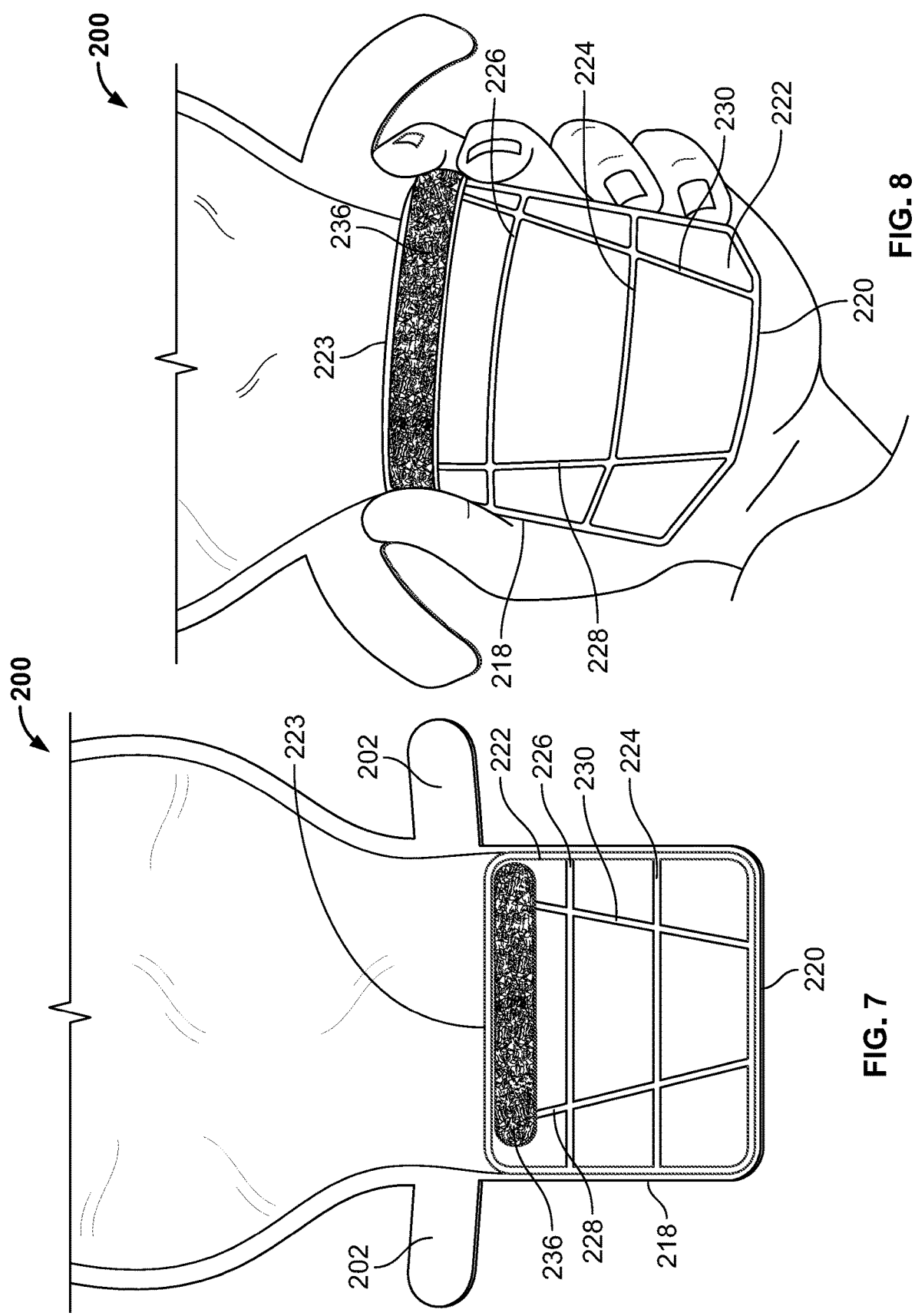

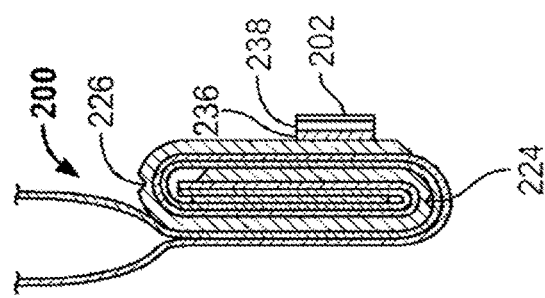
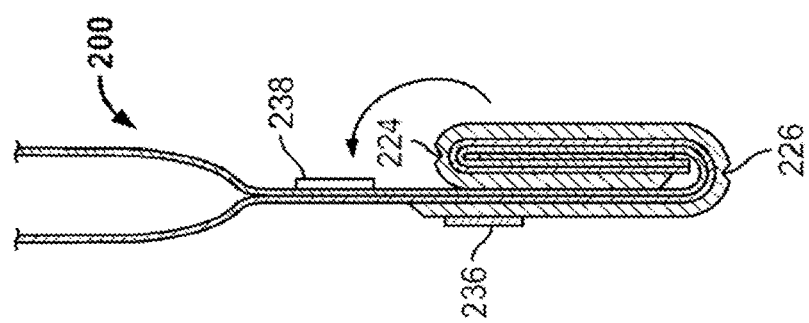
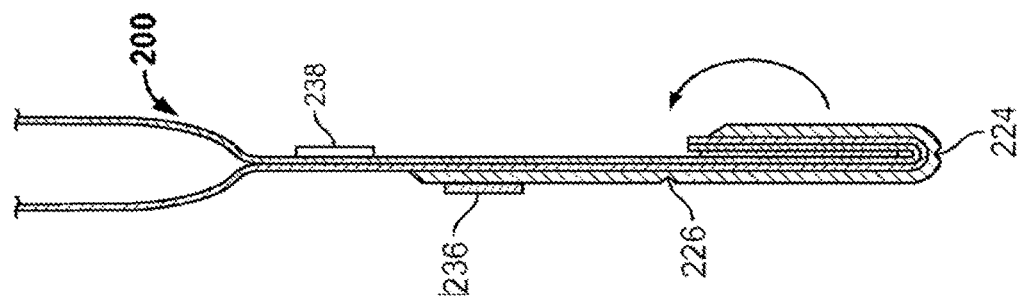
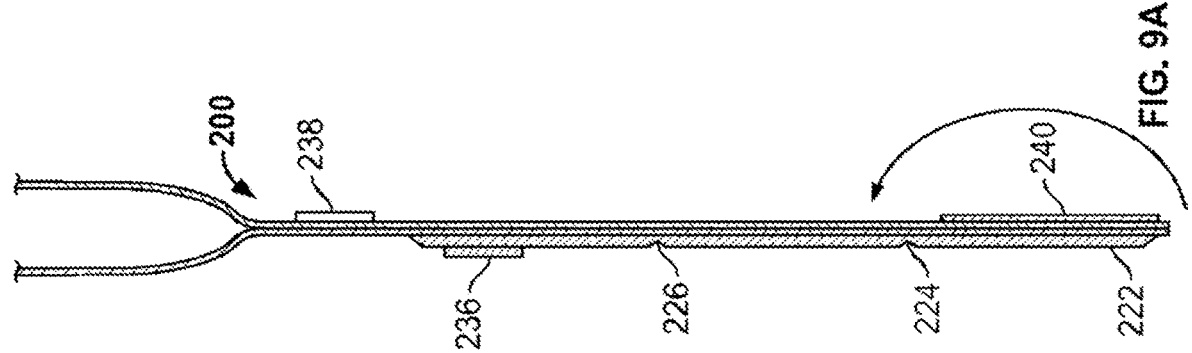

DRAINABLE OSTOMY POUCH

This is a National Stage Application of International Patent Application No. PCT/US2018/014517, filed Jan. 19, 2018, which claims the benefit of and priority to U.S. Provisional Application No. 62/448,612, filed Jan. 20, 2017, the entirety of which are incorporated fully herein by reference.

BACKGROUND

The present disclosure generally relates to ostomy appliances, and more particularly to drainable ostomy pouches having closure systems.

Ostomy pouches for collecting body waste are used by patients who have had surgery such as a colostomy, ileostomy, or urostomy. Ostomy pouches typically include flat, opposing side walls secured together along their edges to define a collection cavity. One of the side walls is provided with an opening to receive a stoma, and means to secure the pouch to the user, such as an adhesive barrier, so that body waste discharged through the stoma is received within the cavity.

The ostomy pouch may be a closed-end pouch for a single use, in which case the entire pouch is discarded after it has been substantially filled with stomal discharge. Alternatively, the ostomy pouch can be a drainable pouch with a discharge opening at its lower end, which may be closed during collection of body waste material but may be opened for draining body waste material from the pouch after a period of use. Such drainable pouches are disclosed, for example, in Nolan, U.S. Pat. No. 3,523,534, and Jensen et al., U.S. Pat. No. 4,411,659, which are incorporated herein in their entirety by reference.

The discharge opening of drainable pouches is typically defined at the end of a narrowed outlet portion, which is provided with closure means for maintaining the discharge opening in a sealed condition until waste material is to be drained from the pouch. The closure means may take the form of a clamp, as in the aforementioned Nolan patent, or a device such as conventional wire ties or wraps for securing the outlet portion in an upwardly-rolled condition.

For quality of life of the users, drainable pouches should be easy to drain without risking soiling of clothes or the surroundings. They also should be easy to close securely after being drained and amenable to being cleaned after drainage and before closing again, such that the risk of unpleasant odor is substantially reduced. Most importantly, the closure means should provide a secure seal when closed to minimize the risk of leakage.

Many different solutions concerning the closing, cleaning and drainage operations have been proposed and implemented. For example, Villefrance et al., U.S. Pat. No. 7,879,015 and Friske et al., U.S. Pat. No. 8,672,907, which are commonly assigned with the present application and incorporated herein in their entirety by reference, disclose drainable pouches having integral closure systems. For obvious reasons, further improvements in the closure systems for easier operation and reduced risk of leakage are much desired by users.

Accordingly, there is a need for an improved closure system for drainable pouches.

BRIEF SUMMARY

A drainable ostomy pouch including a single-piece closure member is provided according to various embodiments. The single-piece closure member may include a plurality of fold-lines to facilitate folding up of an outlet portion for closure and/or opening of a discharge opening.

In one aspect, a drainable ostomy pouch may include a bodyside wall and a distal wall joined along their peripheral edges to define a cavity therebetween for collecting stomal discharge, and a downwardly extending outlet portion terminating in a discharge opening for draining stomal discharge contents collected in the cavity. The outlet portion may include a closure system including a single-piece closure member, which may include at least one transversely-extending fold-line configured to facilitate folding up of the outlet portion. The closure system may be configured such that the outlet portion is folded at least once along the at least one transversely-extending fold-line for closure. Further, the closure system may include a two-part fastening system configured for securing the folded outlet portion in a closed position.

In an embodiment, the single-piece closure member may also include at least one axially-extending fold-line configured to facilitate opening of the discharge opening. The at least one axially-extending fold-line may intersect the at least one transversely-extending fold-line generally perpendicular to each other. The single-piece closure member may be configured to bend along the at least one axially-extending fold-line when pressure is applied along the peripheral edges of the outlet portion to open the discharge opening. In an embodiment, the at least one axially-extending fold-line may include two axially-extending fold-lines, which may be configured to bend outwardly when pressure is applied along the peripheral edges of the outlet portion to open the discharge opening.

In another embodiment, the single-piece closure member may include at least one slanted fold-line configured to facilitate opening of the discharge opening. The at least one slanted fold-line may extend from an upper periphery of the single-piece closure member to a lower periphery of the single-piece closure member proximate the discharge opening, and intersect the at least one transversely-extending fold-line. The single-piece closure member may be configured to bend along the at least one slanted fold-line when pressure is applied along the peripheral edges of the outlet portion to open the discharge opening. In an embodiment, the at least one slanted fold-line may include two slanted fold-lines that are configured such that a distance between the slanted fold-lines proximate the lower periphery is smaller than that of proximate the upper periphery. In another embodiment, the at least one slanted fold-line may include two slanted fold-lines that are configured such that a distance between the slanted fold-lines proximate the lower periphery is greater than that of proximate the upper periphery. The slanted fold-lines may be configured to bend outwardly when pressure is applied along the peripheral edges of the outlet portion to open the discharge opening.

In an embodiment, the single-piece closure member may comprise a first portion including an upper periphery and a lower periphery, in which at least two fold sections are defined in the first section between the upper and lower peripheries and the at least one transversely-extending fold-line. The single-piece closure member may also include a flap. In such an embodiment, the upper periphery of the first portion may be defined by a third transversely-extending line arranged at an intersection of the first portion and the flap. In some embodiments, the first portion may include first and second transversely-extending fold-lines, in which a first fold section is defined between the lower periphery and the first transversely-extending fold-line, and a second fold section is defined between the first and second transversely-extending fold-lines, and a third fold section is defined between the second transversely-extending fold-line and the third transversely-extending line. In such embodiments, the outlet portion may be configured to be folded two times for closure, in which the outlet portion may be folded along the first transversely-extending fold-line for a first fold and folded along the second transversely-extending fold-line for a second fold.

The flap may be configured to rotate up and down about the third transversely-extending line. The two-part fastening system may include a first fastener strip and a second fastener strip, in which the first fastener strip is arranged on an outer surface of the flap, and the second fastener strip may be arranged on an outer surface of the outlet portion opposite the second fold section. In such an embodiment, the ostomy pouch may be configured to be secured in a closed position by engaging the first and second fastener strips after folding the outlet portion two times along the first and second transversely-extending lines.

The single-piece closure member may be arranged on an outer surface of the distal wall in the outlet portion, and the second fastener strip may be arranged on an outer surface of the bodyside wall opposite the second fold section. In such an embodiment, the outlet portion may be configured to be folded along the first transversely-extending fold-line, such that the first and second fold sections abut each other after the first fold. Further, an outer surface of the bodyside wall opposite the first fold section may abut the third fold section after the second fold along the second transversely-extending fold-line. The outlet portion may also be configured such that the second fastener strip is arranged adjacent the flap, such that the first second fastener strips engage each other when the flap rotates downward along the third transversely-extending line to secure the folded outlet in the closed position. Each of the first, second, and third fold sections may have a generally same width.

In another embodiment, the outlet portion may include two-side extensions. In such an embodiment, the two-part fastening system may include one first fastener strip and two second fastener strips. The first fastener strip may be arranged on the single-piece closure member proximate an upper periphery, while each of the two second fastener strips may be arranged on a distal surface of each of the side extensions. The ostomy pouch may be closed by folding the outlet portion at least once along the at least one transversely-extending fold-line and folding the side extensions to engage the first and second fastener strips. In an embodiment, the single-piece closure member may be arrange on a bodyside surface of the outlet portion and include two transversely-extending fold-lines. In such an embodiment, the ostomy pouch may be configured to be closed by folding the outlet portion three times toward a distal surface of ostomy pouch and folding the side extensions toward the distal surface and engaging the first and second fastener strips to secure the outlet portion in a closed position In an embodiment, the single-piece closure member may be attached to the outlet portion via an adhesive. For example the adhesive may be provided on a substantially entire pouch-facing surface of the first portion. Alternatively, the adhesive may be provided in a discontinuous pattern on the pouch-facing surface of the first portion. In an embodiment, at least one transversely-extending fold-line is defined by at least one cut line provided on the pouch facing surface of the first portion, in which the at least one transversely-extending fold-line is devoid of the adhesive. In any of the foregoing embodiment, the single-piece closure member may be formed from a polymeric material.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein:

FIG. 1 is a perspective view of a drainable ostomy pouch including a single-piece closure member according to an embodiment;

FIG. 2 is a perspective view of the drainable ostomy pouch of FIG. 1 in an open position;

FIG. 3 is a perspective view of the drainable ostomy pouch of FIG. 1 showing a fastening member on the opposite side of the single-piece closure member;

FIG. 4 is a perspective view of the drainable ostomy pouch of FIG. 1 rolled-up for closure;

FIG. 7 is a perspective view of a drainable ostomy pouch including a single-piece closure member according to another embodiment;

FIG. 8 is a perspective view of the drainable ostomy pouch of FIG. 7 in an open position;

FIG. 9A is a schematic cross-sectional view of an outlet portion of the drainable ostomy pouch of FIG. 7;

FIG. 9B is a schematic cross-sectional view of the outlet portion of the drainable ostomy pouch of FIG. 7 folded up once;

FIG. 9C is a schematic cross-sectional view of the outlet portion of the drainable ostomy pouch of FIG. 7 folded up two times;

FIG. 9D is a schematic cross-sectional view of the outlet portion of the drainable ostomy pouch of FIG. 7 folded up three times and secured in place with a pair of fastening members;

DETAILED DESCRIPTION

Figure 6A:
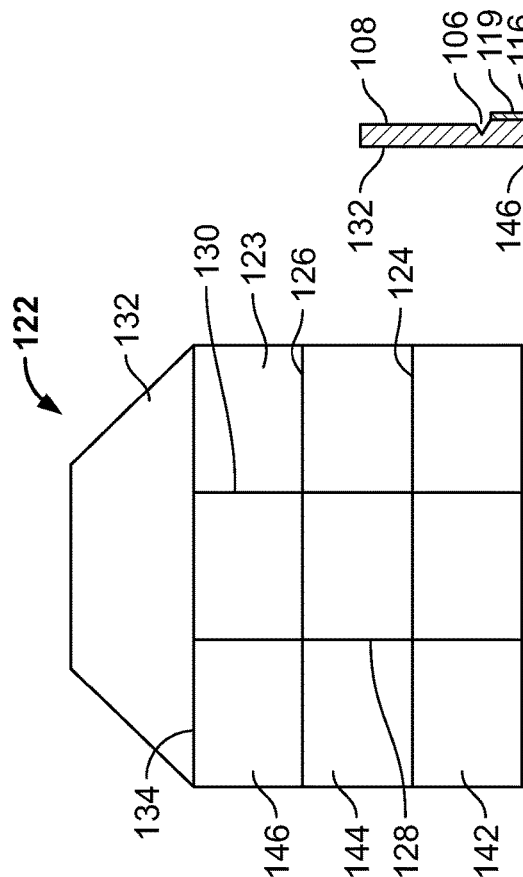
FIG. 6A is a schematic plan view of a single-piece closure member for a drainable ostomy pouch according to an embodiment.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular.

Figure 5:
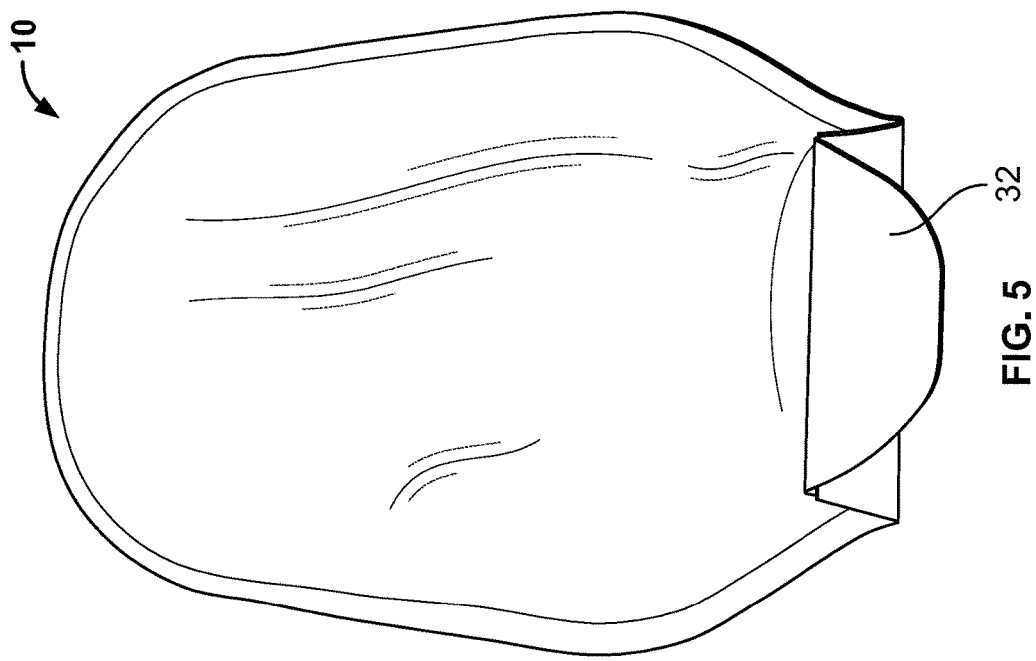
FIG. 5 is a perspective view of the drainable ostomy pouch of FIG. 1 rolled-up and closed via a two-part fastening system.

Referring now to the figures, FIGS. 1-5 show a drainable pouch 10 according to an embodiment. The drainable pouch 10 may include a distal wall 12 and a bodyside wall 14, which may be joined along their peripheral edges 16 to define a cavity therebetween for collecting stomal discharge. The drainable pouch 10 may include a downwardly extending outlet portion 18 terminating in a discharge opening 20 for draining the contents collected in the cavity after a period of use. The discharge opening 20 of the drainable pouch 10 may be closed during use by folding the outlet portion 18 upwardly and securing it in the upwardly folded position as shown in FIGS. 4 and 5.

The walls 12, 14 may be formed of a suitable flexible sheet material, such as a polymeric film, which may be a monolayer or multilayer film. Each of the walls 12, 14 may be formed of one continuous flexible film to define the entire pouch including the outlet portion 18. Alternatively, the walls of the outlet portion 18 may be formed of separate flexible films than the walls of the pouch body. That is, the walls of the outlet portion 18 may be formed of a different polymeric film than the walls of the pouch body.

The drainable pouch 10 may be provided with a single-piece closure member 22 on a distal surface of the outlet portion 18. The single-piece closure member 22 may comprise a first portion 23 including a plurality of fold-lines 24, 26, 28, 30, and a flap 32, which may be integrally formed with the first portion 23. In the embodiment of FIGS. 1-5, the first portion 23 includes two transversely-extending fold-lines 24, 26, and two axially-extending fold-lines 28, 30. The first portion 23 also includes a third transversely-extending line 34 at an intersection of the first portion 23 and the flap 32, such that the flap 32 may be rotated up and down along the third transversely-extending line 34. In other embodiments, the single-piece closure member 22 may include one transversely-extending fold-line or more than two transversely-extending fold-lines, and/or one axially-extending fold-line or more than two axially-extending fold-lines.

The single-piece closure member 22 may be formed from a suitable thin material, such as thin polymeric materials having a thickness of about 2 mil to about 40 mil, preferably about 5 mil to about 20 mil, and more preferably about 8 mil to about 15 mil. For example, the single-piece closure member 22 may be formed by thermal forming, extruding, or molding using a suitable polymer material such as, for example, MYLAR® brand polyester (PET) available from DuPont.

The single-piece closure member 22 may be attached to a distal surface of the distal wall 12 in the outlet portion 18 as shown in FIG. 1. The single-piece closure member 22 may be provided such that a lower periphery 40 of the first portion 23 is arranged proximate the discharge opening 20. The single-piece closure member 22 may be configured to facilitate folding and closing of the outlet portion 18 to provide a liquid tight seal.

In such an embodiment, the transversely-extending fold-lines 24, 26 may be configured to extend generally parallel with the lower periphery 40, spaced apart from each other, such that the outlet portion 18 may be folded along the transversely-extending fold-lines 24, 26 for closure. When closing, the outlet portion 18 may be folded along a first transversely-extending fold-line 24, such that a first fold section 42 of the single-piece closure member 22, which is defined between the first transversely-extending fold-line 24 and the lower periphery 40, abuts a second fold section 44 defined between the first transversely-extending fold-line 24 and a second transversely-extending fold-line 26. Subsequently, the outlet portion 18 may be folded again along the second transversely-extending fold-line 26, such that the bodyside wall 14 in the outlet portion 18 opposite the first fold section 42 abuts a third fold section 46 of the single-piece closure member 22 defined between the second transversely-extending fold-line 26 and the third transversely-extending line 34.

In some embodiments, the single-piece closure member 22 may be positioned, such that the lower periphery 40 is spaced away from the discharge opening 20 to provide bottom portions 41, 43 (FIG. 2) of the pouch walls 12, 14 exposed between the lower periphery 40 and the discharge opening 20. When folding the single-piece closure member 22, the bottom portion 41, 43 may be arranged adjacent the first transversely-extending fold-line 24 and increase folding tension to improve sealing of the single-piece closure member 22 in a folded and closed position. The single-piece closure member 22 may be arranged at a various distance from the discharge opening 20 to provide a desired area of the bottom portions 41, 43 according to the pouch wall thicknesses, single-piece closure member thickness, and single-piece closure member fold-line configuration to obtain a liquid tight seal in a folded and closed position.

The transversely-extending fold-lines 24, 26 and the thickness of the single-piece closure member 22 may be configured to provide adequate sealing tension against the pouch walls 12, 14 when the outlet portion 18 is folded for closure. In the embodiment of FIGS. 1-5, the transversely-extending fold-lines 24, 26 may be arranged generally equal distance apart, such that each of the first, second and third fold sections 42, 44, 46 has a generally same width. In other embodiments, the transversely-extending fold-lines may be arranged at various locations to provide the fold sections having a various width. Further, in some embodiments, the single-piece closure member 22 may include one transversely-extending fold-line providing two fold sections for a single fold closure, or may include more than two transversely-extending fold-lines providing more than three fold sections, in which the outlet portion 18 may be folded three times or more for closure.

The one-piece closure member 22 may also include at least one axially-extending fold-line to facilitate opening of the discharge opening 20 for emptying of stomal discharge. In the embodiment of FIGS. 1-5, the one-piece closure member 22 may include two parallel axially-extending fold-lines 28, 30. To open the discharge opening 20, a user may apply pressure along axially-extending peripheral edges of the outlet portion 18 to fold the one-piece closure member 22 along the axially-extending fold-lines 28, 30 as shown in FIG. 2. In other embodiments, the one-piece closure member 22 may include one axially-extending fold-line or more than two parallel axially-extending fold-lines.

The one-piece closure member 22 including the transversely-extending fold-lines 24, 26 and the axially-extending fold-lines 28, 30 may provide two axis of manipulation including a transverse axis for folding and sealing, and an axial axes for opening of the drainable pouch 10. The transversely-extending fold-lines 24, 26 and the axially-extending fold-lines 28, 30 may be defined by creases or cuts in the one-piece closure member 22. For example, the fold lines may be provided by cutting into the one-piece closure member 22 via any known method, such as via laser cutting or die cutting. Alternatively, the fold lines may be defined by living hinges formed during a molding or extrusion process of the one-piece closure member 22, each of which may comprise creases on both distal surface and pouch-facing surface of the one-piece closure member.

The drainable pouch 10 may also include a two-part fastening system comprising first and second fastener strips 36, 38 for securing the rolled-up outlet portion 18 in a closed position as shown in FIG. 5. The first fastener strip 36 may be provided on a distal surface 48 of the flap 32, while the second fastener strip 38 may be arranged on a distal surface of the bodyside wall 14 in the outlet portion 18. In the embodiment of FIGS. 1-5, the second fastener strip 38 is attached to the distal surface of the bodyside wall 14 in the outlet portion opposite the second fold section 44, such that the second fastener strip 38 may be arranged on the distal wall 12 side of the drainable pouch 10 adjacent the flap 32 after the outlet portion 18 is folded two time as illustrated in FIG. 4. The first and second fastener strips 36, 38 may include fastener elements, which are adapted for releasable interlocking engagement. The flap 32 may be folded down along the third transversely-extending line 34 after the outlet portion 18 is folded to engage the first and second fastener strips 36, 38 to secure the folded outlet portion 18 as shown in FIGS. 4 and 5.

In an embodiment, the first and second fastener strips 36, 38 may comprise a polypropylene material of the type sold under the trademark DUOTEC by G. Binder GmbH & Co. Holzgerlingen, Germany, which is stated in product literature to work on the principle of interlocking mushroom elements. By using this synthetic material for the first and second fastener strips 36, 38, the discharge opening 20 can be maintained in a closed position absent a disengagement force sufficient to overcome the retention force. Further, the interlocking mushroom elements are designed so both strips can be identical, and thus, there is no need to use physically distinguishable male/female components, or to use any fabric-like material that will have a strong tendency to absorb body waste materials and odors and then be difficult to clean.

Among the attributes for this material are its ability to provide a strong and solid connection when pressed firmly together, its characteristic locking action that provides a user with tactile indication of when the fastener strips are interlocked, and its ability to be repeatedly opened and closed. The opening and closing action of fastener strips formed of this material also produces only very limited noise. However, it is to be understood that other type of fastening means may be used, such as, for example, hook and loop fasteners as marketed under the Velcro trademark or pressure sensitive adhesive coatings.

In the embodiment of FIGS. 1-5, the one-piece closure member 22 is provided in the outlet portion 18 on the distal wall 12. In other embodiments, the one-piece closure member 22 may be provided in the outlet portion 18 on the bodyside wall 14.

Figure 6B:
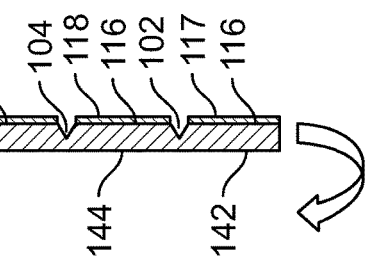
FIG. 6B is a schematic right side view of the single-piece closure member of FIG. 6A.
Figure 6C:
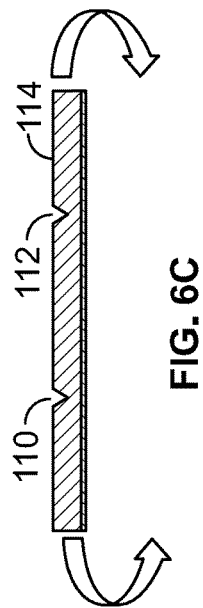
FIG. 6C is a schematic front elevational view of the single-piece member of FIG. 6A.

Referring to FIGS. 6A-6C, a single-piece closure member 122 according to an embodiment is shown. The single-piece closure member 122 may comprise a body 123 including a plurality of fold-lines 124, 126, 128, 130, and a flap 132, which may be integrally formed with the body 123. In the embodiment of FIGS. 6A-6C, the body 123 includes two transversely-extending fold-lines 124, 126, and two axially-extending fold-lines 128, 130. The body 123 also includes a third transversely-extending line 134 at an intersection of the body 123 and the flap 132.

In this embodiment, the transversely-extending fold-lines 124, 126 and the third transversely-extending line 134 are defined by cut lines 102, 104, 106 on a pouch-facing surface 108 of the single-piece closure member 122, in which first, second, third fold sections 142, 144, 146 are provided as shown in FIG. 6B. The axially-extending fold lines 128, 130 are defined by cut lines 110, 112 on a distal surface 114 as shown in FIG. 6C. In other embodiments, the transversely-extending fold-lines may be provided on the distal surface and/or the axially-extending fold-lines may be provided on the pouch-facing surface. In some embodiments, the transversely-extending fold-lines and axially-extending fold-lines may be provided on the same surface. Further, the fold-lines may be defined by crease lines and/or cut lines.

The single-piece closure member 122 may be attached to an outlet portion of an ostomy pouch using a known method, such as via an adhesive, heat sealing, ultrasonic welding, laser welding, etc. For example, the single-piece closure member 122 may be attached to the outlet portion via an adhesive provided on the pouch-facing surface 108 of the body 123. The adhesive may be provided to cover the substantially entire pouch-facing surface 108 of the body 123. Alternatively, the adhesive may be provided in a discontinuous pattern covering a portion of the pouch-facing surface 108 of the body 123.

In the embodiment of FIGS. 6A-6C, an adhesive 116 is provided on a portion of the pouch-facing surface 108 including adhesive areas 117, 118, 119. As shown in FIG. 6B, the pouch-facing surface 108 at and proximate the transversely-extending fold-lines 124, 126 and the third transversely-extending line 134 are not covered with the adhesive 116. Further, the pouch-facing surface 108 of the flap 132 is also not covered with the adhesive.

In such an embodiment, the pouch wall adjacent the adhesive free areas of the single-piece closure member 122 including the transversely-extending fold-lines 124, 126 is not attached to the single-piece closure member 122, and thus may stretch when the single-piece closure member 122 is folded for closure. The placement of the adhesive between the single-piece closure member 122 and the pouch wall, and the configuration of fold-lines, such as a depth of transversely-extending fold-lines 124, 126, may be designed to obtain an adequate tension applied to the pouch films in a folded-up closed position for a liquid tight seal.

FIGS. 7-10 illustrate a drainable ostomy pouch 200 including a single-piece closure member 222 according to another embodiment. The single-piece closure member 222 may be configured similar to the single-piece closure member 22 of FIGS. 1-5, comprising fold-lines 224, 226, 228, 230. The fold-lines may include two transversely-extending fold-lines 224, 226 and two slanted fold-lines 228, 230. The fold-lines 224, 226, 228, 230 may be configured similar to the fold-lines 24, 26, 28, 30 of the single-piece closure member 22, except the slanted fold-lines 228, 230 are sloped, such that the slanted fold-lines 228, 230 do not perpendicularly bisect the transversely-extending fold-lines 224, 226. In the embodiment of FIGS. 7 and 8, the slanted fold-lines 228, 230 are configured such that a distance between the slanted fold-lines 228, 230 proximate a discharge opening 220 is smaller than that of proximate an upper periphery 223. Similar to the axially-extending fold-lines 28, 30, the slanted fold-lines may be configured to facilitate opening of an outlet portion 218.

In an embodiment, the single-piece closure member 222 may be arranged on a bodyside surface of an ostomy pouch 200 in the outlet portion 218. In other embodiments, the single-piece closure member may be arrange on a distal surface of an ostomy pouch. The ostomy pouch 200 may also include side extensions 202, wherein the single-piece closure member 222 may be arranged on the outlet portion 218 between the side extensions 202 and the discharge opening 220 as shown in FIG. 7. The ostomy pouch 200 may include fastening members 236, 238 configured to engage each other to secure the outlet portion 218 in a closed position. The fastening member 236 may be arranged on the single-piece closure member 222 proximate the upper periphery 223 as shown in FIGS. 7 and 8. The fastening member 238 may include two pieces of fasteners, each of which may be arranged on distal side surfaces of each of the side extensions 202 (FIGS. 9A-9D).

To close the outlet portion 218, the single-piece closure member 222 may be folded toward a distal surface of the ostomy pouch 200 along the transversely-extending fold-lines 224, 226. In this embodiment, the ostomy pouch 200 may be configured to be closed by folding up the outlet portion 218 three times and folding the side extensions toward the distal surface to engage the fastening members 236, 238, thereby securing the outlet portion 218 in the closed position as shown in FIGS. 9A-9D. In other embodiments, the ostomy pouch may be configured to be closed after folding up the outlet portion once or twice or more than three times.

Figure 10:
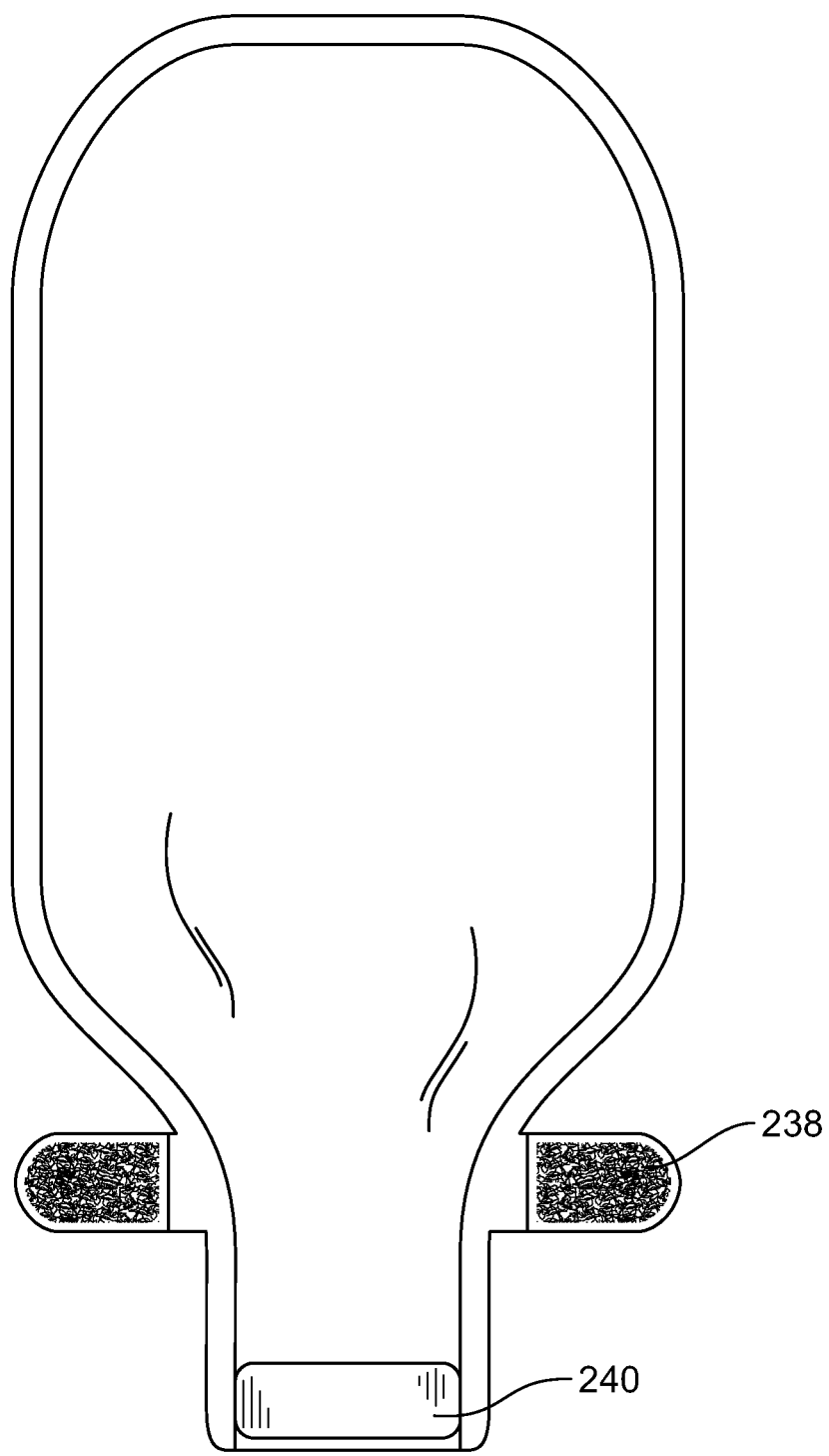
FIG. 10 is a perspective view of the drainable ostomy pouch of FIG. 7 showing fastening members and a stiffening member on the opposite side of the single-piece closure member.

In some embodiments, the drainable ostomy pouch 200 may include an optional stiffening 240 on the opposite side of the single-piece closure member 222 proximate the discharge opening for facilitating opening of the discharge opening as shown in FIGS. 9A-10.

The single-piece closure member according to various embodiments of the present disclosure provides a number of advantages over drainable ostomy pouch closure system including multiple closure members. By configuring the closure system into a sing-piece closure member, required folding tolerances for a liquid-tight seal of an outlet may be built into the transversely-extending fold-lines in the single-piece closure member. Thus, a relatively complex assembly process requiring a high tolerance placement of multiple closure members may be eliminated, rendering a simplified assembly.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A drainable ostomy pouch, comprising: a bodyside wall and a distal wall joined along their peripheral edges to define a cavity therebetween for collecting stomal discharge; a downwardly extending outlet portion terminating in a discharge opening for draining stomal discharge contents collected in the cavity, the outlet portion including a closure system comprising: a single-piece closure member formed separately from the outlet portion and attached to a surface of the outlet portion and including at least one transversely-extending fold-line configured to facilitate folding up of the outlet portion, wherein the closure system is configured such that the outlet portion is folded at least once along the at least one transversely-extending fold-line for closure, wherein the at least one transversely-extending fold-line is defined by at least one crease or cut line to allow the single-piece closure member to bend onto itself at the at least one crease or cut line, wherein the single-piece closure member comprises slanted fold-lines configured to facilitate opening of the discharge opening, wherein the slanted fold-lines consists of axially-extending slanted fold-lines that do not intersect each other any other axially-extending slanted fold-lines and are configured to facilitate opening of the discharge opening, wherein the axially-extending slanted fold-lines continuously extend from an upper periphery of the single-piece closure member to a lower periphery of the single-piece closure member proximate the discharge opening; and a two-part fastening system configured for securing the folded outlet portion in a closed position.

2. The drainable ostomy pouch of claim 1, wherein the axially-extending slanted fold-lines intersects the at least one transversely-extending fold-line, wherein the single-piece closure member is configured to bend along the axially-extending slanted fold-lines when pressure is applied along the peripheral edges of the outlet portion to open the discharge opening.

3. The drainable ostomy pouch of claim 2, wherein the axially-extending slanted fold-lines include consists of two axially-extending slanted fold-lines, wherein the axially-extending slanted fold-lines are configured such that a distance between the axially-extending slanted fold-lines proximate the lower periphery is smaller than that of proximate the upper periphery, wherein the axially-extending slanted fold-lines are configured to bend outwardly when pressure is applied along the peripheral edges of the outlet portion to open the discharge opening.

4. The drainable ostomy pouch of claim 2, wherein the axially-extending slanted fold-lines include consists of two axially-extending slanted fold-lines, wherein the axially-extending slanted fold-lines are configured such that a distance between the axially-extending slanted fold-lines proximate the lower periphery is greater than that of proximate the upper periphery, wherein the axially-extending slanted fold-lines are configured to bend outwardly when pressure is applied along the peripheral edges of the outlet portion to open the discharge opening.

5. The drainable ostomy pouch of claim 1, wherein the single-piece closure member includes a first portion, wherein the first portion includes an upper periphery and a lower periphery, wherein at least two fold sections are defined in the first portion between the upper and lower peripheries and the at least one transversely-extending fold-line.

6. The drainable ostomy pouch of claim 5, wherein the single-piece closure member includes a flap, wherein the upper periphery is defined by a third transversely-extending line arranged at an intersection of the first portion and the flap, and wherein the first portion includes first and second transversely-extending fold-lines, wherein a first fold section is defined between the lower periphery and the first transversely-extending fold-line, and a second fold section is defined between the first and second transversely-extending fold-lines, and a third fold section is defined between the second transversely-extending fold-line and the third transversely-extending line.

7. The drainable ostomy pouch of claim 6, wherein the outlet portion is configured to be folded two times for closure, wherein the outlet portion is folded along the first transversely-extending fold-line for a first fold and folded along the second transversely-extending fold-line for a second fold.

8. The drainable ostomy pouch of claim 7, wherein the flap is configured to rotate up and down about the third transversely-extending line, wherein the two-part fastening system includes a first fastener strip and a second fastener strip, wherein the first fastener strip is arranged on a distal surface of the flap, wherein the second fastener strip is arranged on an outer surface of the outlet portion opposite the second fold section, wherein the ostomy pouch is configured to be secured in the closed position by engaging the first and second fastener strips after folding the outlet portion two times along the first and second transversely-extending lines.

9. The drainable ostomy pouch of claim 8, wherein the single-piece closure member is arranged on a distal surface of the outlet portion, and the second fastener strip is arranged on a bodyside surface of the outlet portion opposite the second fold section, wherein the outlet portion is configured to be folded along the first transversely-extending fold-line, such that the first and second fold sections abut each other after the first fold, and a distal surface of the bodyside wall opposite the first fold section abuts the third fold section after the second fold along the second transversely-extending fold-line, wherein the outlet portion is configured such that the second fastener strip is arranged adjacent the flap, such that the first second fastener strips engage each other when the flap rotates downward along the third transversely-extending line to secure the folded outlet in the closed position.

10. The drainable ostomy pouch of claim 6, wherein each of the first, second, and third fold sections has a generally same width.

11. The drainable ostomy pouch of claim 1, wherein the outlet portion includes two side extensions, wherein the two-part fastening system includes a first fastener strip and two second fastener strips, wherein the first fastener strip is arranged on the single-piece closure member proximate an upper periphery, wherein each of the two second fastener strips is arranged on a distal surface of each of the side extensions, wherein the ostomy pouch is configured to be closed by folding the outlet portion at least once along the at least one transversely-extending fold-lines and folding the side extensions to engage the first and second fastener strips.

12. The drainable ostomy pouch of claim 11, wherein the single-piece closure member is arrange on a bodyside surface of the outlet portion and includes two transversely-extending fold-lines, wherein the ostomy pouch is configured to be closed by folding the outlet portion three times toward a distal surface of ostomy pouch and folding the side extensions toward the distal surface and engaging the first and second fastener strips to secure the outlet portion in a closed position.

13. The drainable ostomy pouch of claim 1, wherein the single-piece closure member is attached to the outlet portion via an adhesive.

14. The drainable ostomy pouch of claim 13, wherein the adhesive is provided on a pouch-facing surface of the single-piece member.

15. The drainable ostomy pouch of claim 14, wherein the at least one transversely-extending fold-line is defined by at least one cut line provided on the pouch facing surface of the single-piece member, wherein the at least one transversely-extending fold-line is devoid of the adhesive.

16. The drainable ostomy pouch of claim 1, wherein the single-piece closure member is formed from a polymeric material.

17. A drainable ostomy pouch, comprising: a bodyside wall and a distal wall joined along their peripheral edges to define a cavity therebetween for collecting stomal discharge; and a downwardly extending outlet portion formed by the bodyside wall and the distal wall and terminating in a discharge opening for draining stomal discharge contents collected in the cavity, the outlet portion including a closure system comprising: a single-piece closure member formed separately from the outlet portion and attached to a surface of the outlet portion and including at least one transversely-extending fold-line, wherein the at least one transversely-extending fold-line is defined by at least one crease or cut line to allow the single-piece closure member to bend onto itself at the at least one crease or cut line and configured to facilitate folding up of the outlet portion, wherein the single-piece closure member comprises at least one axially-extending fold-line that do not intersect any other axially-extending fold-lines and that is configured to facilitate opening of the discharge opening, wherein the at least one axially-extending fold-line intersects the at least one transversely-extending fold-line generally perpendicular to each other, wherein the single-piece closure member is configured to bend along the at least one axially-extending fold-line when pressure is applied along the peripheral edges of the outlet portion to open the discharge opening, wherein the single-piece closure member includes an upper periphery and a lower periphery, wherein at least two fold sections are defined on the single-piece closure member between the upper and lower peripheries and separated by the at least one transversely-extending fold-line, wherein the closure system is configured such that the outlet portion is folded at least once along the at least one transversely-extending fold-line for closure; a stiffening member located on an opposite side of the single-piece closure member proximate the discharge opening; and a two-part fastening system configured for securing the folded outlet portion in a closed position.

18. The drainable ostomy pouch of claim 17, wherein the at least one axially-extending fold-line includes two axially-extending fold-lines, wherein the axially-extending fold-lines are configured to bend outwardly when pressure is applied along the peripheral edges of the outlet portion to open the discharge opening.

* * * * *